(12) United States Patent
Biberger et al.

(10) Patent No.: US 8,507,402 B1
(45) Date of Patent: Aug. 13, 2013

(54) METHOD AND SYSTEM FOR FORMING PLUG AND PLAY METAL CATALYSTS

(75) Inventors: Maximilian A. Biberger, Scottsdale, AZ (US); Stephen Edward Lehman, Jr., Chandler, AZ (US); Robert Matthew Kevwitch, Chandler, AZ (US); Qinghua Yin, Tempe, AZ (US); Jesudos J. Kingsley, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 0 days.

(21) Appl. No.: 12/474,081

(22) Filed: May 28, 2009

Related U.S. Application Data

(62) Division of application No. 12/001,643, filed on Dec. 11, 2007.

(60) Provisional application No. 60/999,057, filed on Oct. 15, 2007.

(51) Int. Cl.
- *B01J 21/00* (2006.01)
- *B32B 15/02* (2006.01)
- *B05D 1/36* (2006.01)
- *B05D 3/02* (2006.01)
- *B05D 3/00* (2006.01)

(52) U.S. Cl.
USPC .......... 502/232; 428/402; 428/403; 427/201; 427/229; 427/398.1

(58) Field of Classification Search
None
See application file for complete search history.

(56) References Cited

U.S. PATENT DOCUMENTS

| | | | |
|---|---|---|---|
| 2,284,554 A | 5/1942 | Beyerstedt | 196/10 |
| 2,419,042 A | 4/1947 | Todd | 202/205 |
| 2,519,531 A | 8/1950 | Worn | 230/95 |
| 2,562,753 A | 7/1951 | Trost | |
| 2,689,780 A | 9/1954 | Rice | 23/106 |
| 3,001,402 A | 9/1961 | Koblin | 73/421.5 |
| 3,067,025 A | 12/1962 | Chisholm | |
| 3,145,287 A | 8/1964 | Siebein et al. | |
| 3,178,121 A | 4/1965 | Wallace, Jr. | |
| 3,179,782 A | 4/1965 | Matvay | |
| 3,313,908 A | 4/1967 | Unger et al. | |

(Continued)

FOREIGN PATENT DOCUMENTS

| | | |
|---|---|---|
| JP | 56-146804 | 11/1981 |
| JP | 61-086815 A | 5/1986 |

(Continued)

OTHER PUBLICATIONS

Kenvin et al., Journal of Catalysis 135, p. 81-91, May 1992.*

(Continued)

*Primary Examiner* — Milton I Cano
*Assistant Examiner* — Sarah A Slifka
(74) *Attorney, Agent, or Firm* — Morrison & Foerster LLP

(57) ABSTRACT

A metal catalyst is formed by vaporizing a quantity of metal and a quantity of carrier forming a vapor cloud. The vapor cloud is quenched forming precipitate nanoparticles comprising a portion of metal and a portion of carrier. The nanoparticles are impregnated onto supports. The supports are able to be used in existing heterogeneous catalysis systems. A system for forming metal catalysts comprises means for vaporizing a quantity of metals and a quantity of carrier, quenching the resulting vapor cloud and forming precipitate nanoparticles comprising a portion of metals and a portion of carrier. The system further comprises means for impregnating supports with the nanoparticles.

18 Claims, 9 Drawing Sheets

(56) References Cited

U.S. PATENT DOCUMENTS

| | | |
|---|---|---|
| 3,401,465 A | 9/1968 | Larwill |
| 3,450,926 A | 6/1969 | Kiernan ........................ 313/231 |
| 3,457,788 A | 7/1969 | Miyajima ....................... 73/422 |
| 3,537,513 A | 11/1970 | Austin ............................ 165/70 |
| 3,741,001 A | 6/1973 | Fletcher et al. .................. 73/28 |
| 3,752,172 A | 8/1973 | Cohen et al. .................... 137/12 |
| 3,774,442 A | 11/1973 | Gustavsson ....................... 73/28 |
| 3,830,756 A | 8/1974 | Sanchez et al. |
| 3,871,448 A | 3/1975 | Vann et al. |
| 3,892,882 A | 7/1975 | Guest et al. |
| 3,914,573 A | 10/1975 | Muehlberger |
| 3,959,420 A | 5/1976 | Geddes et al. ................. 261/112 |
| 3,969,482 A | 7/1976 | Teller |
| 4,008,620 A | 2/1977 | Narato et al. ............ 73/421.5 A |
| 4,018,388 A | 4/1977 | Andrews |
| 4,139,497 A | 2/1979 | Castor et al. |
| 4,157,316 A | 6/1979 | Thompson et al. |
| 4,171,288 A | 10/1979 | Keith et al. |
| 4,174,298 A | 11/1979 | Antos |
| 4,248,387 A | 2/1981 | Andrews |
| 4,284,609 A | 8/1981 | deVries |
| 4,369,167 A | 1/1983 | Weir, Jr. |
| 4,388,274 A | 6/1983 | Rourke et al. |
| 4,431,750 A | 2/1984 | McGinnis et al. |
| 4,436,075 A | 3/1984 | Campbell et al. .............. 123/557 |
| 4,458,138 A | 7/1984 | Adrian et al. |
| 4,505,945 A | 3/1985 | Dubust et al. |
| 4,513,149 A | 4/1985 | Gray et al. |
| 4,731,517 A | 3/1988 | Cheney |
| 4,764,283 A | 8/1988 | Ashbrook et al. |
| 4,765,805 A | 8/1988 | Wahl et al. |
| 4,824,624 A | 4/1989 | Palicka et al. ................... 264/67 |
| 4,855,505 A | 8/1989 | Koll |
| 4,866,240 A | 9/1989 | Webber |
| 4,885,038 A | 12/1989 | Anderson et al. |
| 4,983,555 A | 1/1991 | Roy et al. ....................... 501/120 |
| 4,987,033 A | 1/1991 | Abkowitz et al. ............. 428/469 |
| 5,041,713 A | 8/1991 | Weidman |
| 5,043,548 A | 8/1991 | Whitney et al. .......... 219/121.84 |
| 5,070,064 A | 12/1991 | Hsu et al. |
| 5,073,193 A | 12/1991 | Chaklader et al. .............. 75/346 |
| 5,157,007 A | 10/1992 | Domesle et al. |
| 5,230,844 A | 7/1993 | Macaire et al. |
| 5,338,716 A | 8/1994 | Triplett et al. |
| 5,369,241 A | 11/1994 | Taylor et al. ............. 219/121.47 |
| 5,371,049 A | 12/1994 | Moffett et al. .................. 501/89 |
| 5,372,629 A | 12/1994 | Anderson et al. ............... 75/332 |
| 5,392,797 A | 2/1995 | Welch ........................... 134/108 |
| 5,439,865 A * | 8/1995 | Abe et al. ....................... 502/333 |
| 5,442,153 A | 8/1995 | Marantz et al. |
| 5,460,701 A | 10/1995 | Parker et al. |
| 5,464,458 A | 11/1995 | Yamamoto |
| 5,485,941 A | 1/1996 | Guyomard et al. .............. 222/1 |
| 5,534,149 A | 7/1996 | Birkenbeil et al. |
| 5,553,507 A | 9/1996 | Basch et al. ............. 73/863.01 |
| 5,582,807 A | 12/1996 | Liao et al. |
| 5,611,896 A | 3/1997 | Swanepoel et al. ............ 204/169 |
| 5,630,322 A | 5/1997 | Heilmann et al. ................ 62/95 |
| 5,652,304 A | 7/1997 | Mizrahi |
| 5,726,414 A | 3/1998 | Kitahashi et al. |
| 5,749,938 A | 5/1998 | Coombs .......................... 75/332 |
| 5,776,359 A | 7/1998 | Schultz et al. ............. 252/62.51 |
| 5,788,738 A | 8/1998 | Pirzada et al. ................... 75/331 |
| 5,811,187 A | 9/1998 | Anderson et al. ............. 428/403 |
| 5,837,959 A | 11/1998 | Muehlberger et al. |
| 5,851,507 A | 12/1998 | Pirzada et al. |
| 5,853,815 A | 12/1998 | Muehlberger ................. 427/446 |
| 5,905,000 A | 5/1999 | Yadav et al. ..................... 429/33 |
| 5,935,293 A | 8/1999 | Detering et al. ............. 75/10.29 |
| 5,989,648 A | 11/1999 | Phillips ......................... 427/456 |
| 5,993,967 A | 11/1999 | Brotzman, Jr. et al. ....... 428/407 |
| 5,993,988 A | 11/1999 | Ohara et al. ..................... 429/40 |
| 6,012,647 A | 1/2000 | Ruta et al. .................. 239/132.1 |
| 6,033,781 A | 3/2000 | Brotzman, Jr. et al. ....... 428/405 |
| 6,059,853 A | 5/2000 | Coombs .......................... 75/332 |
| 6,102,106 A | 8/2000 | Manning et al. ................. 165/76 |
| 6,117,376 A | 9/2000 | Merkel |
| 6,213,049 B1 | 4/2001 | Yang |
| 6,214,195 B1 | 4/2001 | Yadav et al. ................... 205/334 |
| 6,228,904 B1 | 5/2001 | Yadav et al. ................... 523/210 |
| 6,254,940 B1 | 7/2001 | Pratsinis et al. .............. 427/562 |
| 6,261,484 B1 | 7/2001 | Phillips et al. .................... 264/5 |
| 6,267,864 B1 | 7/2001 | Yadav et al. ................... 205/341 |
| 6,322,756 B1 | 11/2001 | Arno et al. |
| 6,342,465 B1 | 1/2002 | Klein et al. |
| 6,344,271 B1 | 2/2002 | Yadav et al. ................... 428/402 |
| 6,379,419 B1 | 4/2002 | Celik et al. ...................... 75/346 |
| 6,387,560 B1 | 5/2002 | Yadav et al. ..................... 429/45 |
| 6,395,214 B1 | 5/2002 | Kear et al. ..................... 264/434 |
| 6,398,843 B1 | 6/2002 | Tarrant ............................ 75/249 |
| 6,409,851 B1 | 6/2002 | Sethuram et al. ............. 148/565 |
| 6,413,781 B1 | 7/2002 | Geis et al. |
| 6,416,818 B1 | 7/2002 | Aikens et al. ............... 427/383.1 |
| RE37,853 E | 9/2002 | Detering et al. ............. 75/10.19 |
| 6,444,009 B1 | 9/2002 | Liu et al. |
| 6,475,951 B1 | 11/2002 | Domesle et al. |
| 6,517,800 B1 | 2/2003 | Cheng et al. ................ 423/447.1 |
| 6,524,662 B2 | 2/2003 | Jang et al. ..................... 427/535 |
| 6,531,704 B2 | 3/2003 | Yadav et al. ................. 250/493.1 |
| 6,548,445 B1 | 4/2003 | Buysch et al. |
| 6,554,609 B2 | 4/2003 | Yadav et al. ....................... 432/9 |
| 6,562,304 B1 | 5/2003 | Mizrahi |
| 6,562,495 B2 | 5/2003 | Yadav et al. ..................... 429/12 |
| 6,569,397 B1 | 5/2003 | Yadav et al. ................... 423/345 |
| 6,569,518 B2 | 5/2003 | Yadav et al. ................... 428/323 |
| 6,572,672 B2 | 6/2003 | Yadav et al. ..................... 75/343 |
| 6,579,446 B1 | 6/2003 | Teran et al. |
| 6,596,187 B2 | 7/2003 | Coll et al. |
| 6,603,038 B1 * | 8/2003 | Hagemeyer et al. ........ 560/241.1 |
| 6,607,821 B2 | 8/2003 | Yadav et al. ................... 428/323 |
| 6,610,355 B2 | 8/2003 | Yadav et al. ................... 427/115 |
| 6,623,559 B2 | 9/2003 | Huang ............................ 117/87 |
| 6,635,357 B2 | 10/2003 | Moxson et al. ............... 428/548 |
| 6,641,775 B2 | 11/2003 | Vigliotti et al. ................ 264/618 |
| 6,652,822 B2 | 11/2003 | Phillips et al. ................. 423/290 |
| 6,652,967 B2 * | 11/2003 | Yadav et al. ................... 428/403 |
| 6,669,823 B1 | 12/2003 | Sarkas et al. .................. 204/164 |
| 6,682,002 B2 | 1/2004 | Kyotani ......................... 239/318 |
| 6,689,192 B1 | 2/2004 | Phillips et al. ................... 75/342 |
| 6,699,398 B1 | 3/2004 | Kim ................................ 216/55 |
| 6,706,097 B2 | 3/2004 | Zornes ............................ 96/153 |
| 6,706,660 B2 | 3/2004 | Park |
| 6,710,207 B2 | 3/2004 | Bogan, Jr. et al. |
| 6,713,176 B2 | 3/2004 | Yadav et al. ................... 428/402 |
| 6,716,525 B1 | 4/2004 | Yadav et al. ................... 428/402 |
| 6,746,791 B2 | 6/2004 | Yadav et al. ..................... 429/30 |
| 6,772,584 B2 | 8/2004 | Chun et al. ...................... 60/275 |
| 6,786,950 B2 | 9/2004 | Yadav et al. ..................... 75/346 |
| 6,813,931 B2 | 11/2004 | Yadav et al. ................... 73/31.05 |
| 6,817,388 B2 | 11/2004 | Tsangaris et al. ............... 141/82 |
| 6,832,735 B2 | 12/2004 | Yadav et al. ..................... 241/16 |
| 6,838,072 B1 | 1/2005 | Kong et al. .................. 423/594.2 |
| 6,855,426 B2 | 2/2005 | Yadav .......................... 428/403 |
| 6,855,749 B1 | 2/2005 | Yadav et al. ................... 523/105 |
| 6,886,545 B1 | 5/2005 | Holm ....................... 123/568.21 |
| 6,896,958 B1 | 5/2005 | Cayton et al. ................. 428/323 |
| 6,902,699 B2 | 6/2005 | Fritzemeier et al. ............ 419/38 |
| 6,916,872 B2 | 7/2005 | Yadav et al. ................... 524/430 |
| 6,919,527 B2 | 7/2005 | Boulos et al. ............ 219/121.52 |
| 6,933,331 B2 | 8/2005 | Yadav et al. ................... 523/210 |
| 6,972,115 B1 | 12/2005 | Ballard |
| 6,986,877 B2 | 1/2006 | Takikawa et al. .......... 423/447.3 |
| 6,994,837 B2 * | 2/2006 | Boulos et al. ................. 423/613 |
| 7,007,872 B2 | 3/2006 | Yadav et al. ..................... 241/1 |
| 7,022,305 B2 | 4/2006 | Drumm et al. |
| 7,052,777 B2 | 5/2006 | Brotzman, Jr. et al. ........ 428/570 |
| 7,073,559 B2 | 7/2006 | O'Larey et al. ............. 164/76.1 |
| 7,081,267 B2 | 7/2006 | Yadav ........................... 427/115 |
| 7,101,819 B2 | 9/2006 | Rosenflanz et al. ............ 501/10 |
| 7,147,544 B2 | 12/2006 | Rosenflanz ..................... 451/28 |
| 7,147,894 B2 | 12/2006 | Zhou et al. .................... 427/256 |
| 7,166,198 B2 | 1/2007 | Van Der Walt et al. ........ 204/165 |
| 7,166,663 B2 | 1/2007 | Cayton et al. ................. 524/430 |
| 7,172,649 B2 | 2/2007 | Conrad et al. .................. 106/35 |

| | | |
|---|---|---|
| 7,172,790 B2 | 2/2007 | Koulik et al. |
| 7,178,747 B2 | 2/2007 | Yadav et al. ............... 241/23 |
| 7,208,126 B2 | 4/2007 | Musick et al. ............ 423/69 |
| 7,211,236 B2 | 5/2007 | Stark et al. ............ 423/592.1 |
| 7,217,407 B2 | 5/2007 | Zhang ..................... 423/610 |
| 7,220,398 B2 | 5/2007 | Sutorik et al. |
| 7,307,195 B2 | 12/2007 | Polverejan et al. ......... 585/443 |
| 7,323,655 B2 | 1/2008 | Kim .................. 219/121.43 |
| 7,384,447 B2 | 6/2008 | Kodas et al. ............ 75/332 |
| 7,417,008 B2 | 8/2008 | Richards et al. |
| 7,494,527 B2 | 2/2009 | Jurewicz et al. |
| 7,541,012 B2 | 6/2009 | Yeung et al. |
| 7,541,310 B2 | 6/2009 | Espinoza et al. |
| 7,572,315 B2 | 8/2009 | Boulos et al. |
| 7,611,686 B2 | 11/2009 | Alekseeva et al. |
| 7,615,097 B2 | 11/2009 | McKechnie et al. |
| 7,618,919 B2 | 11/2009 | Shimazu et al. |
| 7,622,693 B2 | 11/2009 | Foret |
| 7,678,419 B2 | 3/2010 | Kevwitch et al. |
| 7,803,210 B2 | 9/2010 | Sekine et al. |
| 7,897,127 B2 | 3/2011 | Layman et al. |
| 7,905,942 B1 | 3/2011 | Layman |
| 8,051,724 B1 | 11/2011 | Layman et al. |
| 8,076,258 B1 | 12/2011 | Biberger |
| 8,142,619 B2 | 3/2012 | Layman et al. |
| 2001/0042802 A1 | 11/2001 | Youds |
| 2002/0018815 A1 | 2/2002 | Sievers et al. ............... 424/489 |
| 2002/0068026 A1 | 6/2002 | Murrell et al. |
| 2002/0079620 A1 | 6/2002 | DuBuis et al. ............ 264/328.14 |
| 2002/0100751 A1 | 8/2002 | Carr |
| 2002/0102674 A1 | 8/2002 | Anderson ................ 435/174 |
| 2002/0131914 A1 | 9/2002 | Sung |
| 2002/0143417 A1 | 10/2002 | Ito et al. |
| 2002/0182735 A1 | 12/2002 | Kibby et al. |
| 2002/0192129 A1 | 12/2002 | Shamouilian et al. |
| 2003/0036786 A1 | 2/2003 | Duren et al. ............ 607/96 |
| 2003/0042232 A1 | 3/2003 | Shimazu |
| 2003/0066800 A1 | 4/2003 | Saim et al. ............... 264/5 |
| 2003/0108459 A1 | 6/2003 | Wu et al. ............ 422/186.04 |
| 2003/0139288 A1 | 7/2003 | Cai et al. |
| 2003/0172772 A1 | 9/2003 | Sethuram et al. |
| 2003/0223546 A1 | 12/2003 | McGregor et al. ............ 378/143 |
| 2004/0009118 A1 | 1/2004 | Phillips et al. |
| 2004/0023302 A1 | 2/2004 | Archibald et al. |
| 2004/0023453 A1 | 2/2004 | Xu et al. ................ 257/369 |
| 2004/0077494 A1 | 4/2004 | LaBarge et al. |
| 2004/0103751 A1 | 6/2004 | Joseph et al. ............... 75/10.19 |
| 2004/0119064 A1 | 6/2004 | Narayan et al. |
| 2004/0127586 A1 | 7/2004 | Jin et al. |
| 2004/0167009 A1 | 8/2004 | Kuntz et al. ............ 501/95.2 |
| 2004/0176246 A1 | 9/2004 | Shirk et al. |
| 2004/0208805 A1 | 10/2004 | Fincke et al. |
| 2004/0213998 A1* | 10/2004 | Hearley et al. ............... 428/402 |
| 2004/0251017 A1 | 12/2004 | Pillion et al. ............ 165/289 |
| 2004/0251241 A1 | 12/2004 | Blutke et al. |
| 2005/0000321 A1 | 1/2005 | O'Larey et al. ............ 75/952 |
| 2005/0000950 A1 | 1/2005 | Schroder et al. ......... 219/121.59 |
| 2005/0066805 A1 | 3/2005 | Park et al. |
| 2005/0077034 A1 | 4/2005 | King ..................... 165/163 |
| 2005/0097988 A1 | 5/2005 | Kodas et al. ............ 75/332 |
| 2005/0106865 A1 | 5/2005 | Chung et al. |
| 2005/0163673 A1 | 7/2005 | Johnson et al. |
| 2005/0199739 A1 | 9/2005 | Kuroda et al. |
| 2005/0220695 A1 | 10/2005 | Abatzoglou et al. |
| 2005/0227864 A1 | 10/2005 | Sutorik et al. |
| 2005/0233380 A1 | 10/2005 | Pesiri et al. ............... 435/7.1 |
| 2005/0240069 A1 | 10/2005 | Polverejan et al. ............ 585/444 |
| 2005/0258766 A1 | 11/2005 | Kim .................. 315/111.21 |
| 2005/0275143 A1 | 12/2005 | Toth |
| 2006/0051505 A1 | 3/2006 | Kortshagen et al. ......... 427/212 |
| 2006/0068989 A1 | 3/2006 | Ninomiya et al. |
| 2006/0094595 A1 | 5/2006 | Labarge |
| 2006/0096393 A1 | 5/2006 | Pesiri ..................... 73/863.21 |
| 2006/0105910 A1* | 5/2006 | Zhou et al. ............... 502/338 |
| 2006/0108332 A1 | 5/2006 | Belashchenko ......... 219/121.47 |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. ....... 422/151 |
| 2006/0166809 A1 | 7/2006 | Malek et al. |
| 2006/0222780 A1 | 10/2006 | Gurevich et al. |
| 2006/0231525 A1 | 10/2006 | Asakawa et al. ............... 216/56 |
| 2007/0048206 A1 | 3/2007 | Hung et al. ............... 423/335 |
| 2007/0049484 A1 | 3/2007 | Kear et al. |
| 2007/0063364 A1 | 3/2007 | Hsiao et al. ............... 264/5 |
| 2007/0084308 A1 | 4/2007 | Nakamura et al. |
| 2007/0084834 A1 | 4/2007 | Hanus et al. ............... 219/121.5 |
| 2007/0087934 A1 | 4/2007 | Martens et al. ............... 502/214 |
| 2007/0163385 A1 | 7/2007 | Takahashi et al. |
| 2007/0173403 A1 | 7/2007 | Koike et al. ............... 502/300 |
| 2007/0178673 A1 | 8/2007 | Gole et al. |
| 2007/0253874 A1 | 11/2007 | Foret |
| 2007/0292321 A1 | 12/2007 | Plischke et al. |
| 2008/0006954 A1 | 1/2008 | Yubuta et al. |
| 2008/0031806 A1 | 2/2008 | Gavenonis et al. |
| 2008/0038578 A1 | 2/2008 | Li |
| 2008/0064769 A1 | 3/2008 | Sato et al. |
| 2008/0105083 A1 | 5/2008 | Nakamura et al. |
| 2008/0116178 A1 | 5/2008 | Weidman |
| 2008/0138651 A1 | 6/2008 | Doi et al. |
| 2008/0175936 A1 | 7/2008 | Tokita et al. |
| 2008/0206562 A1 | 8/2008 | Stucky et al. |
| 2008/0207858 A1 | 8/2008 | Kowaleski et al. ............ 526/176 |
| 2008/0274344 A1 | 11/2008 | Vieth et al. |
| 2008/0277092 A1 | 11/2008 | Layman et al. |
| 2008/0277264 A1 | 11/2008 | Sprague |
| 2008/0277266 A1 | 11/2008 | Layman |
| 2008/0277267 A1* | 11/2008 | Biberger et al. ......... 204/157.15 |
| 2008/0277268 A1 | 11/2008 | Layman |
| 2008/0277269 A1 | 11/2008 | Layman et al. |
| 2008/0277270 A1 | 11/2008 | Biberger et al. |
| 2008/0277271 A1 | 11/2008 | Layman |
| 2008/0280049 A1 | 11/2008 | Kevwitch et al. |
| 2008/0280751 A1 | 11/2008 | Harutyunyan et al. |
| 2008/0280756 A1 | 11/2008 | Biberger |
| 2009/0010801 A1 | 1/2009 | Murphy et al. |
| 2009/0054230 A1 | 2/2009 | Veeraraghavan et al. |
| 2009/0088585 A1 | 4/2009 | Schammel et al. |
| 2009/0114568 A1 | 5/2009 | Trevino et al. |
| 2009/0162991 A1 | 6/2009 | Beneyton et al. |
| 2009/0168506 A1 | 7/2009 | Han et al. |
| 2009/0170242 A1 | 7/2009 | Lin et al. |
| 2009/0181474 A1 | 7/2009 | Nagai |
| 2009/0200180 A1 | 8/2009 | Capote et al. |
| 2009/0253037 A1 | 10/2009 | Park et al. |
| 2009/0274903 A1 | 11/2009 | Addiego |
| 2009/0286899 A1 | 11/2009 | Hofmann et al. |
| 2010/0089002 A1 | 4/2010 | Merkel |
| 2010/0275781 A1 | 11/2010 | Tsangaris |
| 2011/0006463 A1 | 1/2011 | Layman |
| 2011/0143041 A1 | 6/2011 | Layman et al. |
| 2011/0143915 A1 | 6/2011 | Yin et al. |
| 2011/0143916 A1 | 6/2011 | Leamon |
| 2011/0143926 A1 | 6/2011 | Yin et al. |
| 2011/0143930 A1 | 6/2011 | Yin et al. |
| 2011/0143933 A1 | 6/2011 | Yin et al. |
| 2011/0144382 A1 | 6/2011 | Yin et al. |
| 2011/0174604 A1 | 7/2011 | Duesel et al. |
| 2011/0247336 A9 | 10/2011 | Farsad et al. |
| 2012/0045373 A1 | 2/2012 | Biberger |
| 2012/0171098 A1 | 7/2012 | Hung et al. |

FOREIGN PATENT DOCUMENTS

| | | |
|---|---|---|
| JP | 63-214342 A | 9/1988 |
| JP | 5228361 A | 9/1993 |
| JP | 5324094 A | 12/1993 |
| JP | 6-065772 A | 9/1994 |
| JP | 7031873 A | 2/1995 |
| JP | H11-502760 A | 3/1999 |
| JP | 2000-220978 A | 8/2000 |
| JP | 2004-233007 A | 8/2004 |
| JP | 2004-249206 A | 9/2004 |
| JP | 2004-290730 A | 10/2004 |
| JP | 2005-503250 A | 2/2005 |
| JP | 2005-122621 A | 5/2005 |
| JP | 2005-218937 A | 8/2005 |
| JP | 2005-342615 A | 12/2005 |
| JP | 2006-001779 A | 1/2006 |
| JP | 2006-508885 A | 3/2006 |

| JP | 2006-247446 A | 9/2006 |
| JP | 2006-260385 A | 9/2006 |
| SU | 493241 | 3/1976 |
| TW | 201023207 | 6/2010 |
| WO | 9628577 A1 | 9/1996 |
| WO | WO 02/092503 A1 | 11/2002 |
| WO | 2004052778 A2 | 6/2004 |
| wo | 2006079213 A1 | 8/2006 |
| WO | WO 2006/079213 A1 | 8/2006 |
| WO | WO-2008/130451 A2 | 10/2008 |
| WO | WO-2008/130451 A3 | 10/2008 |

OTHER PUBLICATIONS

J. Heberlein, "New Approaches in Thermal Plasma Technology"., vol. 74, No. 3, Jan. 2002, pp. 327-335, Pure Appl. Chem.

T. Yoshida, "The Future of Thermal Plasma Processing for Coating", vol. 66, No. 6, Jan. 1994 pp. 1223-1230, Pure & Appl. Chem., Great Britain.

A. Gutsch et al., "Gas-Phase Production of Nanoparticles", Kona No. 20, Jan. 2002, pp. 24-37, Degussa AG.

Dr. Heike Mühlenweg et al., "Gas-Phase Reactions—Open Up New Roads to Nanoproducts", Degussa ScienceNewsletter No. 08, Jan. 2004, pp. 12-16.

"Coating Generation: Vaporization of Particles in Plasma Spraying and Splat Formation", M. Verdelle, A. Vardelle, K-I Ii, P. Fauchais Universite de Limoges, 123 Avenue A. Thomas 87000, Limoges, F., Pure & Chem, vol. 68, No. 5, pp. 1093-1099, Jan. 1996.

H. Konrad et al., "Nanostructured Cu-Bi Alloys Prepared by Co-Evaporation in a Continuous Gas Flow," NanoStructured Materials, vol. 7, No. 6, pp. 605-610, Jan. 1996.

M.Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-301.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

Kenvin et al. "Supported Catalysts Prepared from Monouclear Copper Complexes: Catalytic Properties", Journal of Catalysis, pp. 81-91.

Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670 &DOC=FILE.PDF., 6 pages.

United States Patent and Trademark Office, Office Action, mailed Feb. 19, 2010, U.S. Appl. No. 12/152,109, filed May 9, 2008, First Named Inventor: Maximilian A. Biberger, 17 pages.

United States Patent and Trademark Office, Advisory Action, Mailed: Mar. 4, 2010, U.S. Appl. No. 12/001,643, filed Dec. 11, 2007, First Named Inventor Maximilian A. Biberger, pp. 9.

United States Patent and Trademark Ofice, Office Action, Mailed: Jun. 16, 2010, U.S. Appl. No. 12/001,643, filed Dec. 11, 2007, First Named Inventor: Maximilian A. Biberger, 8 pages.

United States Patent and Trademark Office, Office Action, Mailed: Jun. 9, 2010, U.S. Appl. No. 12/001,602, filed Dec. 11, 2007, First Named Inventor: Maximilian A. Biberger, 10 pages.

United States Patent and Trademark Office, Office Action mailed Oct. 7, 2010, for U.S Appl. No. 12/001,643, pp. 1-15.

United States Patent and Trademark Office, Office Action mailed Oct. 14, 2010, for U.S Appl. No. 12/001,602, pp. 1-13.

Derwent English Abstract for Publication No. SU 193241 A, Application No. 1973SU1943286 filed on Jul. 2, 1973, published on Mar. 1, 1976, entitled" Catalyst for Ammonia Synthesis Contains Oxides of Aluminium, Potassium, Calcium, Iron and Nickel Oxide for Increased Activity," 3 pgs.

Nagai, Yasutaka, et al., "Sintering Inhibition Mechanism of Platinum Supported on Ceria-based Oxide and Pt-oxide-support Interaction," Journal of Catalysis 242 (2006), pp. 103-109, Jul. 3, 2006, Elsevier.

Bateman James E. et al., "Alkylation of Porous Silicon by Direct Reaction with Alkenes and Alkynes," Angew. Chem Int. Ed., Dec. 17, 1998, 37, No. 19, pp. 2683-2685.

Langner, Alexander et al., "Controlled Silicon Surface Functionalization by Alkene Hydrosilylation," J. Am. Chem. Soc., Aug. 25, 2005, 127, pp. 12798-12799.

Liu, Shu-Man et al., "Enhanced Photoluminescence from Si Nano-organosols by Functionalization with Alkenes and Their Size Evolution," Chem. Mater., Jan. 13, 2006, 18, pp. 637-642.

Fojtik, Anton, "Surface Chemistry of Luminescent Colloidal Silicon Nanoparticles," J. Phys. Chem. B., Jan. 13, 2006, pp. 1994-1998.

Li, Dejin et al., "Environmentally Responsive "Hairy" Nanoparticles: Mixed Homopolymer Brushes on Silica Nanoparticles Synthesized by Living Radical Polymerization Techniques," J.Am. Chem. Soc., Apr. 9, 2005, 127, pp. 6248-6256.

Neiner, Doinita, "Low-Temperature Solution Route to Macroscopic Amounts of Hydrogen Terminated Silicon Nanoparticles," J. Am. Chem. Soc., Aug. 5, 2006, 128, pp. 11016-11017.

Fojtik, Anton et al., "Luminescent Colloidal Silicon Particles," Chemical Physics Letters 221, Apr. 29, 1994, pp. 363-367.

Netzer, Lucy et al., "A New Approach to Construction of Artificial Monolayer Assemblies," J. Am. Chem. Soc., 1983, 105, pp. 674-676.

Chen, H.-S. et al., "On the Photoluminescence of Si Nanoparticles," Mater. Phys. Mech. 4, Jul. 3, 2001, pp. 62-66.

Kwon, Young-Soon et al., "Passivation Process for Superfine Aluminum Powders Obtained by Electrical Explosion of Wires," Applied Surface Science 211, Apr. 30, 2003, pp. 57-67.

Liao, Ying-Chih et al., "Self-Assembly of Organic Monolayers on Aerosolized Silicon Nanoparticles," J.Am. Chem. Soc., Jun. 27, 2006, 128, pp. 9061-9065.

Zou, Jing et al., "Solution Synthesis of Ultrastable Luminescent Siloxane-Coated Silicon Nanoparticles," Nano Letters, Jun. 4, 2004, vol. 4, No. 7, pp. 1181-1186.

Tao, Yu-Tai, "Structural Comparison of Self-Assembled Monolayers of n-Alkanoic Acids on the surfaces of Silver, Copper, and Aluminum," J. Am. Chem. Soc., May 1993, 115, pp. 4350-4358.

Sailor, Michael et al., "Surface Chemistry of Luminescent Silicon Nanocrystallites," Adv. Mater, 1997, 9, No. 10, pp. 783-793.

Li, Xuegeng. et al. "Surface Functionalization of Silicon Nanoparticles Produced by Laser-Driven Pyrolysis of Silane Followed by HF-HNO3 Etching," Langmuir, May 25, 2004, pp. 4720-4727.

Carrot, Geraldine et al. "Surface-Initiated Ring-Opening Polymerization: A Versatile Method for Nanoparticle Ordering," Macromolecules, Sep. 17, 2002, 35, pp. 8400-8404.

Jouet R. Jason et al., "Surface Passivation of Bare Aluminum Nanoparticles Using Perfluoroalkyl Carboxylic Acids," Chem. Mater., Jan. 25, 2005, 17, pp. 2987-2996.

Yoshida, Toyonobu, "The Future of Thermal Plasma Processing for Coating," Pure & Appl. Chem., vol. 66, No. 6, 1994, pp. 1223-1230.

Kim, Namyong Y. et al., "Thermal Derivatization of Porous Silicon with Alcohols," J. Am. Chem. Soc., Mar. 5, 1997, 119, pp. 2297-2298.

Hua, Fengjun et al., "Organically Capped Silicon Nanoparticles with Blue Photoluminescence Prepared by Hydrosilylation Followed by Oxidation," Langmuir, Mar. 2006, pp. 4363-4370.

United States Patent and Trademark Office, Office Action mailed Jun. 22, 2011, for U.S. Appl. No. 12/001,643, 13 pgs.

United States Patent and Trademark Office, Office Action mailed Jun. 22, 2011, for U.S. Appl. No. 12/001,602, 15 pgs.

United States Patent and Trademark Office, Office Action mailed Jun. 21, 2011, for U.S. Appl. No. 12/001,644, 12 pgs.

Stiles, A.B., Catalyst Supports and Supported Catalysts, Manufacture of Carbon-Supported Metal Catalysts, pp. 125-132, published Jan. 1, 1987, Butterworth Publishers, 80 Montvale Ave., Stoneham, MA 02180.

Advisory action dated Sep. 23, 2011, U.S. Appl. No. 12/001,643, filed Dec. 11, 2007, Applicant: Maximilian A. Biberger, 8 pages.

U.S. Appl. No. 13/291,983, filed Nov. 8, 2011, for Layman et al.

U.S. Appl. No. 12/152,084, filed May 9, 2008, for Biberger.

U.S. Appl. No. 13/028,693, filed Feb. 16, 2011, for Biberger.

U.S. App. No. 12/943,909, filed Nov. 10, 2010, for Layman.

U.S. Appl. No. 12/152,111, filed May 9, 2008, for Biberger et al.

U.S. Appl. No. 12/151,830, filed May 8, 2008, for Biberger et al.
U.S. Appl. No. 12/968,248, filed Dec. 14, 2010, for Biberger.
U.S. Appl. No. 12/968,245, filed Dec. 14, 2010, for Biberger.
U.S. Appl. No. 12/968,241, filed Dec. 14, 2010, for Biberger.
U.S. Appl. No. 12/968,239, filed Dec. 14, 2010, for Biberger.
U.S. Appl. No. 12/969,128, filed Dec. 15, 2010, for Biberger.
U.S. Appl. No. 12/962,463, filed Dec. 7, 2010, for Leamon.
U.S. Appl. No. 12/961,200, filed Dec. 6, 2010, for Lehman.
U.S. Appl. No. 12/961,108, filed Dec. 6, 2010, for Lehman.
U.S. Appl. No. 12/961,030, filed Dec. 6, 2010, for Lehman.
U.S. Appl. No. 12/968,253, filed Dec. 14, 2010, for Biberger.
U.S. Appl. No. 12/968,235, filed Dec. 14, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,087, filed Dec. 15, 2010, for Biberger.
U.S. Appl. No. 12/962,533, filed Dec. 7, 2010, for Yin et al.
U.S. Appl. No. 12/962,523, filed Dec. 7, 2010, for Yin et al.
U.S. Appl. No. 12/001,643, filed Dec. 11, 2007, for Biberger et al.
U.S. Appl. No. 12/474,081, filed May 28, 2009, for Biberger al.
U.S. Appl. No. 12/001,602, filed Dec. 11, 2007, for Biberger et al.
U.S. Appl. No. 12/001,644, filed Dec. 11, 2007, for Biberger et al.
U.S. Appl. No. 12/969,503, filed Nov. 15, 2010, for Leamon et al.
U.S. Appl. No. 12/969,457, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.
U.S. Appl. No. 13/033,514, filed Feb. 23, 2011, for Biberger et al.
Final Office Action dated Nov. 25, 2011, U.S. Appl. No. 12/001,602, filed Dec. 11, 2007, Maximilian A. Biberger et al.,16 pages.
Office Action dated Oct. 26, 2011, U.S. Appl. No. 12/151,804, filed May 8, 2008, Maximilian A. Biberger et al., 8 pages.
Final Office Action dated Jan. 4, 2012, U.S. Appl. No. 12/001,644, filed Dec. 11, 2007, Maximilian A. Biberger et al., 14 pages.
Final Office Action dated Dec. 29, 2011, U.S. Appl. No. 12/152,109, filed May 9, 2008, Maximilian A. Biberger, 21 pages.
Office Action dated Jun. 7, 2012, U.S. Appl. No. 12/962,518, filed Dec. 7, 2010, Qinghua Yin et al., 10 pages.
Final Office Action dated Jul. 11, 2012, U.S. Appl. No. 12/152,096, filed May 9, 2008, Maximilian A. Biberger et al., 8 pages.
Office Action dated Jul. 18, 2012, U.S. Appl. No. 13/289,955, filed Nov. 4, 2011, Maximilian A. Biberger, 8 pages.
Foreign Office Action dated Jan. 31, 2012, U.S. Appl. No. 2010-508396, SDC Materials, Inc., 5 pages.
Foreign Office Action dated Jan. 25, 2012, Application No. 2010-508374, SDC Materials, Inc., 7 pages
Foreign Office Action dated Jan. 31, 2012, Application No. 2010-508378, SDC Materials, Inc., 6 pages.
Foreign Office dated Mar. 13, 2012, Application No. 2010-508398, SDC Materials, Inc., 3 pages.
Foreign Office Action dated Mar. 13, 2012, Application No. 2010-508373, SDC Materials, Inc., 3 pages.
Kenvin et al. "Supported Catalysts Prepared from Monuclear Copper Complexes: Catalytic Properties", Journal of Catalysis, pp. 81-91, 1992.
National Aeronautics and Space Administration, "Enthalpy", http://www.grc.nasa.gov/WWW/K-12/airplane/enthalpy.html, Nov. 23, 2009, 1 page.
U.S. Appl. No. 13/589,024, filed Aug. 17, 2012, for Yin at al.

* cited by examiner

METHOD AND SYSTEM FOR FORMING PLUG AND PLAY METAL CATALYSTS

RELATED APPLICATION(S)

This Application is a divisional application claiming the benefit of priority from co-pending U.S. patent application Ser. No. 12/001,643, filed on Dec. 11, 2007, and entitled "METHOD AND SYSTEM FOR FORMING PLUG AND PLAY METAL CATALYSTS." The co-pending U.S. patent application Ser. No. 12/001,643, filed on Dec. 11, 2007, and entitled "METHOD AND SYSTEM FOR FORMING PLUG AND PLAY METAL CATALYSTS" is hereby incorporated by reference.

This patent Application claims priority under 35 U.S.C. §119(e) of the U.S. Provisional Patent Application Ser. No. 60/999,057, filed Oct. 15, 2007, and entitled "Nano Particle Catalysts" and which is hereby incorporated by reference in its entirety.

BACKGROUND OF THE INVENTION

In the oil refining and fine chemical industries, catalysts are required to transform one chemical or one material into another. For example, to make cyclohexane from benzene, benzene is passed through porous ceramic supports that have been impregnated with catalysts designed and configured to hydrogenate it into cyclohexane. In one particular process, platinum is nitrated and impregnated onto supports in the wet chemical process 100 shown in FIG. 1. A platinum group metal, such as platinum, osmium, ruthenium, rhodium, palladium or iridium, is collected in step 101. For the sake of brevity, platinum will be discussed herein but it will be apparent to those of ordinary skill in the art that different platinum group metals can be used to take advantage of their different properties. Since blocks of elemental platinum are not useable as a catalyst, the platinum is nitrated in the step 102, forming a salt, specifically $PtNO_3$. The nitration is typically performed using well known methods of wet chemistry. The $PtNO_3$ is dissolved into a solvent such as water in a step 103, causing the $PtNO_3$ to dissociate into Pt+ and $NO_3-$ ions. In the step 104, the salt is adsorbed onto the surfaces of supports 104B through transfer devices 104A, such as pipettes. An example of a support 104B is shown in FIG. 2. Generally, a support 104B is a highly porous ceramic material that is commercially available in a vast array of shapes, dimensions and pore sizes to accommodate particular requirements of a given application. The supports 104B are dried to remove water then transferred to an oven for an air calcining step 105. In the oven, the supports 104B are exposed to heat and optionally pressure that causes the Pt+ to coalesce into elemental Pt particles on the surfaces of the supports 104B. In the step 106, end product catalysts are formed. The end product is a support 104B that is impregnated with elemental platinum. These supports are generally used in catalytic conversion by placing them in reactors of various configurations. For example, benzene is passed through the supports 104B which convert the benzene into cyclohexane in the fine chemical industry. In the oil refining industry, the supports are used in a similar fashion. The process steps are used to convert crude oil into a useable fuel or other desirable end product. The process described in FIG. 1 has opportunities for improvement. Although the platinum sticks sufficiently well to the surface of the support 104b, platinum atoms begin to move and coalesce into larger particles at the temperatures that catalysis generally occurs. It is understood that the effectiveness and activity of a catalyst are directly proportional to the size of the catalyst particles on the surface of the support. As the particles coalesce into larger clumps, the particle sizes increase, the surface area of the catalyst decreases and the effectiveness of the catalyst is detrimentally affected. As the effectiveness of the catalyst decreases, the supports 104B must be removed from the reactors and new supports added. During the transition period, output is stopped and overall throughput is adversely affected. Also, platinum group metal catalysts are very expensive, and every addition of new supports comes at great cost. What is needed is a plug and play catalyst that is usable in current oil refineries and fine chemical processing plants, allowing an increase in throughput and decrease in costs.

SUMMARY OF THE INVENTION

A method of making a metal catalyst comprises providing a quantity of nanoparticles, wherein at least some of the nanoparticles comprise a first portion comprising catalyst material bonded to a second portion comprising a carrier, providing a quantity of supports and impregnating the supports with the nanoparticles. In some embodiments, the supports comprise pores and voids. Preferably, the catalyst material comprises any among a list of at least one metal, at least one metal alloy, at least one metal compound, and any combination thereof. Preferably, providing a quantity of nanoparticles comprises loading a quantity of catalyst material and a quantity of carrier into a plasma gun in a desired ratio, vaporizing the quantity of catalyst material and quantity of carrier thereby forming a vapor cloud, and quenching the vapor cloud, thereby forming a quantity of nanoparticles. In some embodiments, the carrier comprises an oxide, such as silica, alumina, yttria, zirconia, titania, ceria, baria, and any combination thereof. Preferably, impregnating the supports comprises suspending the nanoparticles in a solution, thereby forming a suspension and mixing the suspension with a quantity of the supports. Alternatively, impregnating the supports comprises suspending the nanoparticles in a solution, thereby forming a suspension and mixing the suspension with a slurry having supports suspended therein. In some embodiments, the suspension further comprises a dispersant and/or surfactant. The slurry comprises any one of organic solvent, aqueous solvent, and a combination thereof. The method further comprises drying the supports. Preferably, the method further comprises exposing the supports to any one of heat, pressure and a combination thereof, thereby bonding the nanoparticles onto the porous supports.

A system for forming a metal catalyst comprises means for providing a quantity of nanoparticles, wherein at least some of the nanoparticles comprise a first portion of catalyst material bonded to a second portion of carrier, means for collecting the nanoparticles, means for forming a suspension by mixing the nanoparticles into a liquid, and means for combining the suspension with a quantity of supports, thereby impregnating the supports with the suspension.

Preferably, the supports comprise voids and pores. The catalyst material comprises any among a list of at least one metal, at least one metal alloy, at least one metal compound, and any combination thereof. Preferably, the carrier comprises an oxide, such as silica, alumina, yttria, zirconia, titania, ceria, baria, and any combination thereof. The means for forming a suspension further comprises means for including a dispersant. The system further comprises means for drying the supports. Preferably, the means for providing a quantity of nanoparticles comprises means for loading a quantity of catalyst material and a quantity of carrier into a plasma gun in a desired ratio, means for vaporizing the catalyst material and carrier in a reaction chamber, thereby forming a vapor cloud, and means for quenching the vapor cloud thereby forming solid nanoparticles. The system further comprises means for exposing the supports to heat, pressure, and a combination thereof, thereby bonding the nanoparticles onto the supports. Preferably, the means for combining the suspension with supports comprises means for impregnating supports with the suspension. Alternatively, the means for combining the suspension with supports comprises means for mixing the suspension with a slurry having supports suspended therein. The slurry comprises any among a list of an organic solvent, an aqueous solvent, and any combination thereof.

BRIEF DESCRIPTION OF THE DRAWINGS

The invention is better understood by reading the following detailed description of an exemplary embodiment in conjunction with the accompanying drawings.

DETAILED DESCRIPTION OF THE INVENTION

Reference will now be made in detail to implementations of the present invention as illustrated in the accompanying drawings. The drawings may not be to scale. The same reference indicators will be used throughout the drawings and the following detailed description to refer to identical or like elements. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application, safety regulations and business related constraints, and that these specific goals will vary from one implementation to another and from one developer to another. Moreover, it will be appreciated that such a development effort will be a routine undertaking of engineering for those of ordinary skill in the art having the benefit of this disclosure.

The following description of the invention is provided as an enabling teaching which includes the best currently known embodiment. One skilled in the relevant arts, including but not limited to chemistry and physics, will recognize that many changes can be made to the embodiment described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present inventions are possible and may even be desirable in certain circumstances, and are a part of the present invention. Thus, the following description is provided as illustrative of the principles of the present invention and not in limitation thereof, since the scope of the present invention is defined by the claims. The terms "nanoparticle," "nanoparticle powder," and "nano powder" are generally understood by those of ordinary skill to encompass a quantity of material comprising particles on the order of nanometers in diameter, as described herein.

Figure 3:
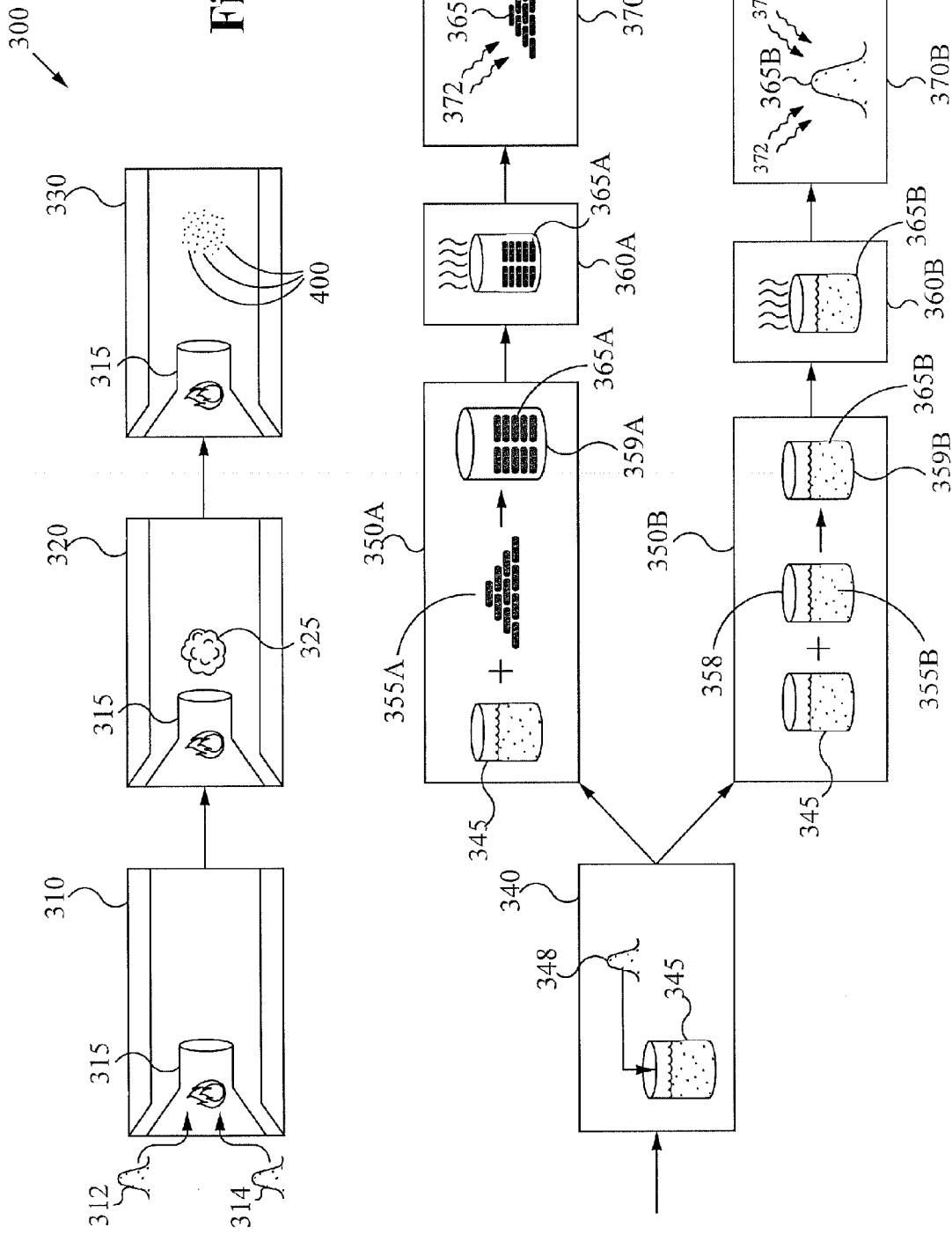
FIG. 3 shows the preferred embodiment of a novel process for forming a support for use in heterogeneous catalysis.

FIG. 3 illustrates the inventive steps for a process 300 of forming a "plug and play" catalyst for use in such industries as chemical reforming and oil refining. The method begins at step 310. A quantity of a catalyst material 312 is loaded into a plasma gun 315, preferably in powder form. Alternatively, the catalyst material 312 is able to be a catalyst precursor. Preferably, the catalyst material 312 comprises a platinum group metal (PGM). The platinum group is a collective name sometimes used for six metallic elements clustered together in the periodic table. The six PGMs are ruthenium, rhodium, palladium, osmium, iridium, and platinum. In some definitions of the PGM group, gold and silver are included. The PGMs have similar physical and chemical properties, and tend to occur together in the same mineral deposits. The PGMs also have excellent catalytic properties. Although PGMs are described, all metals are contemplated. Other metals, such as transition metals and poor metals also exhibit catalytic properties. Generally, transition metals comprise scandium, titanium, chromium, vanadium, manganese, iron, cobalt, nickel, copper, zinc, yttrium, zirconium, niobium, molybdenum, cadmium, tantalum, tungsten, and mercury. Poor metals comprise aluminum, germanium, gallium, tin, antimony, lead, indium, tellurium, bismuth and polonium. The catalyst material 312 is able to comprise more than one starting metal. By way of example, the material 312 is a single alloy comprising multiple metals. Alternatively, the catalyst material 312 comprises multiple homogenous metals. Particularly, metals are used in heterogeneous catalysis. Heterogeneous catalysts provide a surface for the chemical reaction to take place on or an activation point for chemical reactions. Also, in step 310, a quantity of carrier material 314 is loaded into the plasma gun 315, preferably in powder form. In some embodiments, the carrier material 314 is an oxide. By way of example, oxides such as Alumina ($Al_2O_3$), Silica ($SiO_2$), Zirconia ($ZrO_2$), Titania ($TiO_2$), Ceria ($CeO_2$) Baria (BaO), and Yttria ($Y_2O_3$) can be used. Other useful oxides will be apparent to those of ordinary skill. In some embodiments, the catalyst material 312 and carrier material 314 are loaded manually into a hopper (not shown) which automatically loads the materials into the plasma gun 315. In alternate embodiments, an automated system is able to load the catalyst material 312 and oxide carrier 314 into the plasma gun 315. The ratio of the PGM to the carrier can be adjusted to meet particular demands of a given application. Next, in step 320, the plasma gun 315 vaporizes the catalyst material 312 along with the carrier 314 to form a vapor cloud 325. The vapor cloud will comprise both the catalyst material, for example PGM, and the carrier in the ratio that was loaded into the plasma gun 315 in step 310.

Figure 4A:
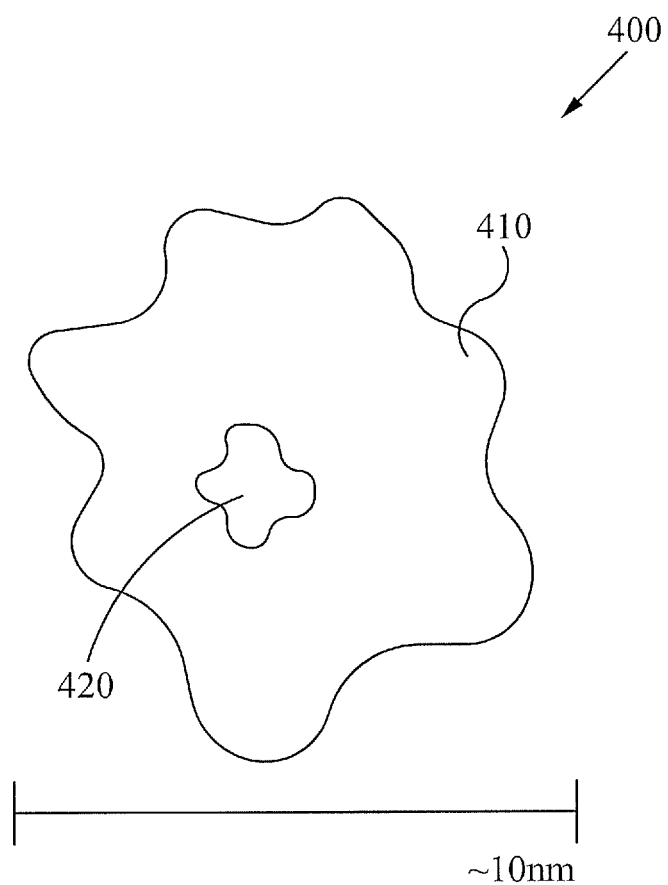
FIG. 4A shows an example of a nanoparticle formed as part of the process of FIG. 3.

Still referring to FIG. 3, the resulting vapor cloud 325 is then put through a quenching step 330. Preferably, the quenching step occurs in a highly turbulent quench chamber to facilitate rapid, even, consistent quenching of the vapor 325 into precipitate nanoparticles 400. Such a rapid quench chamber is described in detail in U.S. patent application Ser. No. 12/151,935, which is hereby incorporated by reference. In some embodiments, the highly turbulent quench chamber comprises a frusto-conical body having a wide end, a narrow end, and a quench region formed between the wide end and the narrow end. The quench chamber also includes a reactive mixture inlet configured to receive a reactive mixture and to supply the reactive mixture into the quench region in the direction of the narrow end. The quench chamber further comprises at least one conditioning fluid inlet configured to supply a conditioning fluid into the quench region in the direction of the narrow end. The frusto-conical body is configured to produce a turbulent flow within the quench region with the supply of the conditioning fluid into the quench region, thereby promoting the quenching of the reactive mixture with the conditioning fluid to form a cooled gas-particle mixture. A gas-particle mixture outlet is disposed at the narrow end. The outlet is configured to receive the cooled gas-particle mixture from the quench region. A conditioning fluid flows into the quench region through at least one conditioning fluid inlet along a plurality of conditioning momentum vectors from the wide end to the narrow end. This flow of conditioning fluid into the quench region forms a turbulent flow within the quench region. The conditioning fluid and the reactive mixture are mixed within the turbulent flow of the quench region, thereby quenching the reactive mixture with the conditioning fluid to form a cooled gas-particle mixture. The cooled gas-particle mixture is flown out of an outlet at the narrow end of the quench region. This cooled gas-particle mixture comprises a plurality of particles entrained in a fluid. In some embodiments, the supply of conditioning fluid into the quench region is configured to produce a flow having a Reynolds Number of at least 1000. In some embodiments, the frusto-conical body is configured to supply the conditioning fluid to the quench region along a plurality of momentum vectors, and at least two of the plurality of momentum vectors form an angle between them that is greater than or equal to 90 degrees. In some embodiments, the reactive mixture inlet is configured to supply the reactive mixture into the quench region along a first momentum vector, the frusto-conical body is configured to supply the conditioning fluid to the quench region along a second momentum vector, and the second momentum vector has an oblique angle greater than 20 degrees relative to the first momentum vector. As the gaseous PGM and carrier cool, they solidify into nanoparticles. An example of a resulting nanoparticle 400 is shown in FIG. 4A. As shown, the nanoparticle comprises a portion of carrier 410, and a portion of catalyst material 420, such as PGM. The ratio of size between the PGM catalyst 420 and carrier 410 will generally be determined by the ratio of the starting quantities of the catalyst material 312 and carrier 314 in step 310 of FIG. 3. The particles 400 will generally be in the range of 0.5 to 200 nm in size, and can be as small as a molecular length of the catalyst portion 420 and as large as would be achievable by ball milling. The particle size is able to be varied with varying starting materials, vaporization speeds, quench speeds and plasma temperatures.

Figure 6:
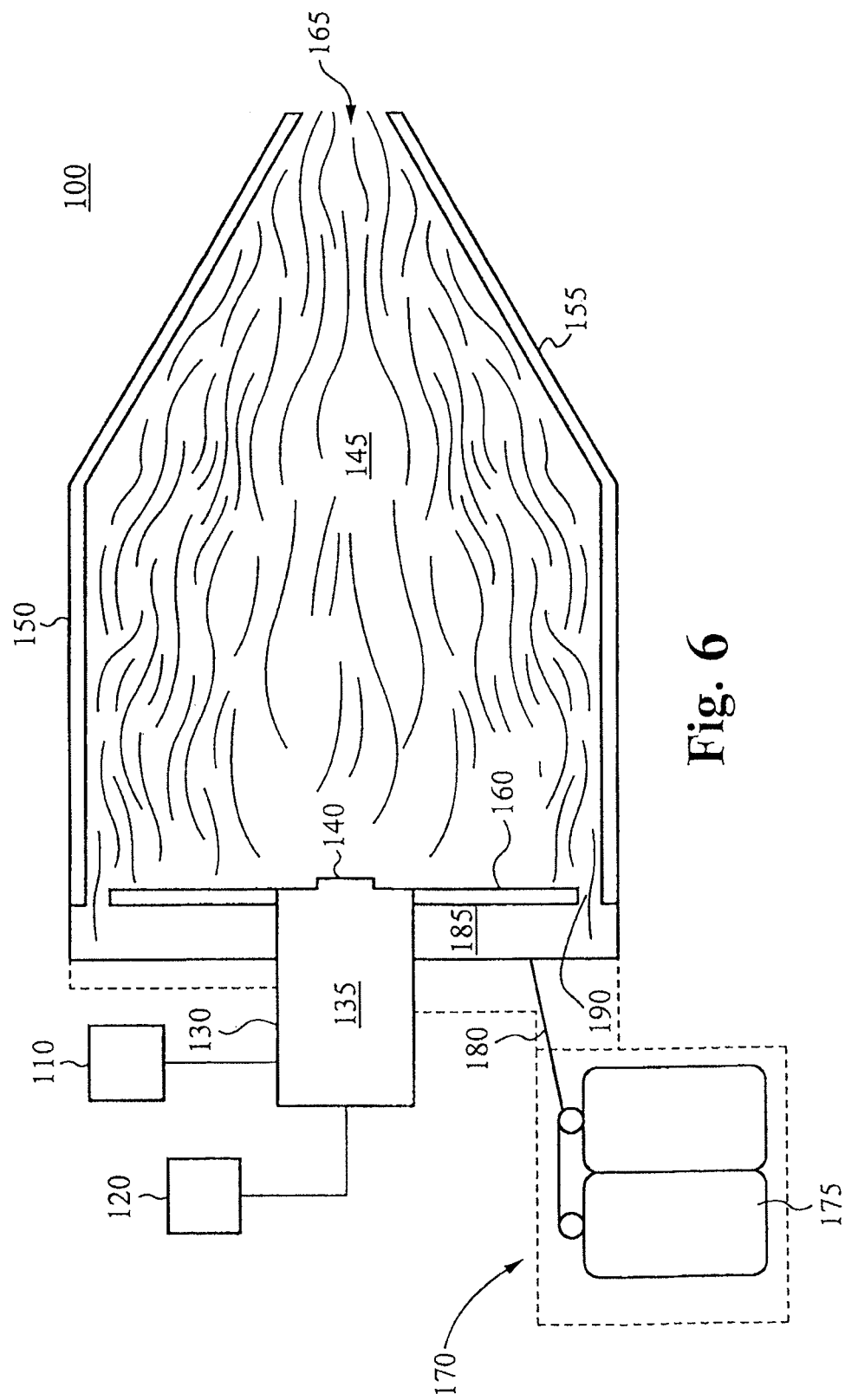
FIG. 6 is a cross-sectional view of one embodiment of a particle production system in accordance with the principles of the present invention.

Details of the quench-chamber will now be described with respect to FIGS. 6 and 7. Referring now to FIG. 6, a gas phase particle production system 100 is presented. The system 100 comprises a precursor supply device 110 and a working gas supply device 120 both fluidly coupled to a plasma production chamber 130 having an energy delivery zone 135 formed therein. The plasma production chamber 130 is fluidly coupled with an injection port 140 of a constricting quench chamber 145, thereby allowing the energy delivery zone 135 to fluidly communicate with the quench chamber 145. One or more ports 190 also allow fluid communication of the quench chamber 145 with a controlled atmosphere system 170 (indicated by the dotted lines). The quench chamber 145 is also fluidly coupled with an ejection port 165.

The reactive mixture flows from the energy delivery zone 135 into the constricting quench chamber 145 through the injection port 140. As the hot mixture moves from the energy delivery zone 135, it expands rapidly within the quench chamber 145 and cools. While the mixture flows into the quench chamber 145, the ports 190 supply conditioning fluid along the inner surfaces of the quench chamber 145. The conditioning fluid combines, at least to some extent, with the mixture, and flows from the quench chamber 145 through the ejection port 165.

During a period immediately after entering the quench chamber 145, particle formation occurs. Furthermore, the supply of conditioning fluid along the inner surfaces of the quench chamber 145 works to condition the reactive mixture, to maintain entrainment of the particles therein, and to prevent the depositing of material on the inner surfaces of the quench chamber 145.

Still referring to FIG. 6, the structure of the quench chamber 145 can be formed of relatively thin walled components capable of dissipating substantial heat. For example, the thin-walled components can conduct heat from inside the chamber and radiate the heat to the ambient. The quench chamber 145 comprises a substantially cylindrical surface 150, a cone-like (frusto-conical) surface 155, and an annular surface 160 connecting the injection port 140 with the cylindrical surface 150. The cylindrical surface 150, having a large diameter relative to the size of the injection port 140, provides accommodation for the expansion of the reactive mixture that occurs after the mixture flows into the quench chamber 145. The cone-like surface 155 extends from the cylindrical surface 150, away from the injection port 140 and towards the ejection port 165. The cone-like surface 155 is sufficiently smoothly varying so as to not unduly compress fluid flowing from through the quench chamber 145 to the ejection port 165.

Substantial heat is emitted, mostly in the form of radiation, from the mixture following its entry into the quench chamber 145. The quench chamber 145 is preferably designed to dissipate this heat efficiently. For example, the surfaces of the quench chamber 145 are preferably exposed to a cooling apparatus (not shown).

Still referring to FIG. 6, the controlled atmosphere system 170 preferably comprises a chamber 185 into which conditioning fluid is introduced from a reservoir 175 through a conduit 180. The conditioning fluid preferably comprises argon. However, other inert, relatively heavy gases are equally preferred. Furthermore, the preferable mechanism of providing the conditioning fluid into the quench chamber 145 is the formation of a pressure differential between the quench chamber 145 and the outlet 165. Such pressure differential will draw the conditioning fluid into the quench chamber 145 through the ports 190. Other less preferred methods of providing the conditioning fluid include, but are not limited to, forming positive pressure within the chamber 185.

The frusto-conical shape of the quench chamber 145 can provide a modest amount of turbulence within the quench region, thereby promoting the mixing of the conditioning fluid with the reactive mixture, and increasing the quenching rate beyond prior art systems. However, in some situations, an even greater increase in quenching rate may be desired. Such an increase in quenching rate can be achieved by creating a highly turbulent flow within a region of a quench chamber where the conditioning fluid is mixed with the reactive mixture.

Figure 7:
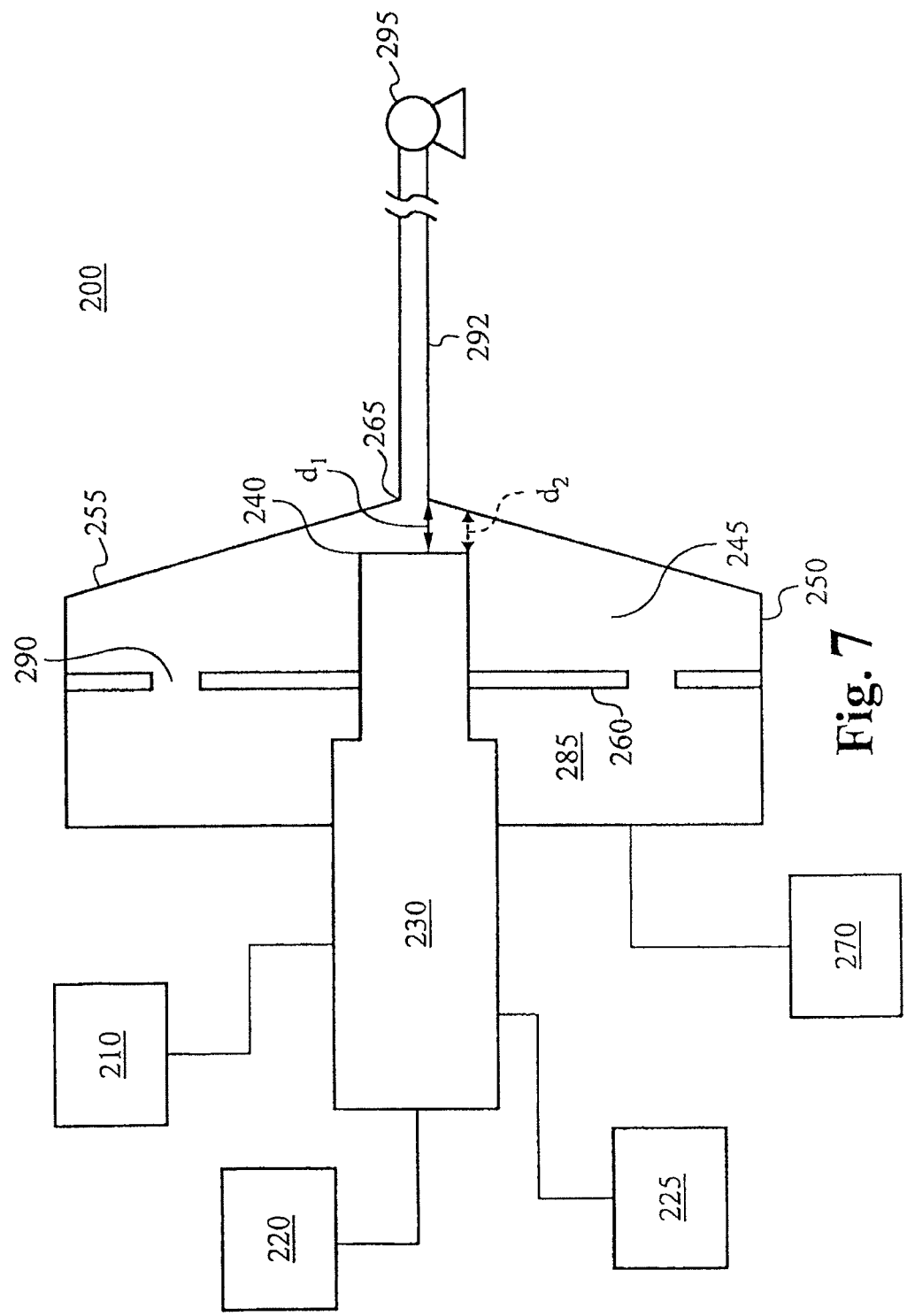
FIG. 7 is a cross-sectional view of one embodiment of a particle production system with a highly turbulent quench chamber in accordance with the principles of the present invention.

FIG. 7 illustrates a gas phase particle production system 200 with a highly turbulent quench chamber 245. The system 200 comprises a precursor supply device 210 a working gas supply device 220 fluidly coupled to a plasma production and reaction chamber 230, similar to plasma production chamber 130 discussed above with reference to FIG. 6. An energy delivery system 225 is also coupled with the plasma production and reactor chamber 230. The plasma production and reactor chamber 230 includes an injection port 240 that communicates fluidly with the constricting quench chamber 245. One or more ports 290 can also allow fluid communication between the quench chamber 245 and a controlled atmosphere system 270, similar to controlled atmosphere system 170 in FIG. 6. The quench chamber 245 is also fluidly coupled to an outlet 265.

Generally, the chamber 230 operates as a reactor, similar to chamber 130 in FIG. 6, producing an output comprising particles within a gas stream. Production includes the basic steps of combination, reaction, and conditioning as described later herein. The system combines precursor material supplied from the precursor supply device 210 and working gas supplied from the working gas supply device 220 within the energy delivery zone of the chamber 230. The system energizes the working gas in the chamber 230 using energy from the energy supply system 225, thereby forming a plasma. The plasma is applied to the precursor material within the chamber 230 to form an energized, reactive mixture. This mixture comprises one or more materials in at least one of a plurality of phases, which may include vapor, gas, and plasma. The reactive mixture flows from the plasma production and reactor chamber 230 into the quench chamber 245 through an injection port 240.

The quench chamber 245 preferably comprises a substantially cylindrical surface 250, a frusto-conical surface 255, and an annular surface 260 connecting the injection port 240 with the cylindrical surface 250. The frusto-conical surface 255 narrows to meet the outlet 265. The plasma production and reactor chamber 230 includes an extended portion at the end of which the injection port 240 is disposed. This extended portion shortens the distance between the injection port 240 and the outlet 265, reducing the volume of region in which the reactive mixture and the conditioning fluid will mix, referred to as the quench region. In a preferred embodiment, the injection port 240 is arranged coaxially with the outlet 265. The center of the injection port is positioned a first distance $d_1$ from the outlet 265. The perimeter of the injection port is positioned a second distance $d_2$ from a portion of the frusto-conical surface 255. The injection port 240 and the frusto-conical surface 255 form the aforementioned quench region therebetween. The space between the perimeter of the injection port 240 and the frusto-conical surface 255 forms a gap therebetween that acts as a channel for supplying conditioning fluid into the quench region. The frusto-conical surface 255 acts as a funneling surface, channeling fluid through the gap and into the quench region.

While the reactive mixture flows into the quench chamber 245, the ports 290 supply conditioning fluid into the quench chamber 245. The conditioning fluid then moves along the frusto-conical surface 255, through the gap between the injection port 240 and the frusto-conical surface 255, and into the quench region. In some embodiments, the controlled atmosphere system 270 is configured to control the volume flow rate or mass flow rate of the conditioning fluid supplied to the quench region.

As the reactive mixture moves out of the injection port 240, it expands and mixes with the conditioning fluid. Preferably, the angle at which the conditioning fluid is supplied produces a high degree of turbulence and promotes mixing with the reactive mixture. This turbulence can depend on many parameters. In a preferred embodiment, one or more of these parameters is adjustable to control the level of turbulence. These factors include the flow rates of the conditioning fluid, the temperature of the frusto-conical surface 255, the angle of the frusto-conical surface 255 (which affects the angle at which the conditioning fluid is supplied into the quench region), and the size of the quench region. For example, the relative positioning of the frusto-conical surface 255 and the injection port 240 is adjustable, which can be used to adjust the volume of quench region. These adjustments can be made in a variety of different ways, using a variety of different mechanisms, including, but not limited to, automated means and manual means.

During a brief period immediately after entering the quench chamber 245, particle formation occurs. The degree to which the particles agglomerate depends on the rate of cooling. The cooling rate depends on the turbulence of the flow within the quench region. Preferably, the system is adjusted to form a highly turbulent flow, and to form very dispersed particles. For example, in preferred embodiments, the turbidity of the flow within the quench region is such that the flow has a Reynolds Number of at least 1000.

Still referring to FIG. 7, the structure of the quench chamber 245 is preferably formed of relatively thin walled components capable of dissipating substantial quantities of heat. For example, the thin-walled components can conduct heat from inside the chamber and radiate the heat to the ambient.

Substantial heat is emitted, mostly in the form of radiation, from the reactive mixture following its entry into the quench chamber 245. The quench chamber 245 is designed to dissipate this heat efficiently. The surfaces of the quench chamber 245 are preferably exposed to a cooling system (not shown). In a preferred embodiment, the cooling system is configured to control a temperature of the frusto-conical surface 255.

Following injection into the quench region, cooling, and particle formation, the mixture flows from the quench chamber 245 through the outlet port 265. Suction generated by a generator 295 moves the mixture and conditioning fluid from the quench region into the conduit 292. From the outlet port 265, the mixture flows along the conduit 292, toward the suction generator 295. Preferably, the particles are removed from the mixture by a collection or sampling system (not shown) prior to encountering the suction generator 295.

Still referring to FIG. 7, the controlled atmosphere system 270 comprises a chamber 285, fluidly coupled to the quench region through port(s) 290, into which conditioning fluid is introduced from a reservoir. For example, as shown in FIG. 6 the conditioning fluid can be introduced through conduit 180 from reservoir 175. As described above, the conditioning fluid preferably comprises argon. However, other inert, relatively heavy gases are equally preferred. Also, as discussed above, the preferable mechanism of providing the conditioning fluid into the quench chamber 245 is the formation of a pressure differential between the quench chamber 245 and the outlet 265. Such pressure differential will draw the conditioning fluid into the quench chamber 245 through the ports 290. Other methods of providing the conditioning fluid include, but are not limited to, forming positive pressure within the chamber 285.

U.S. Pat. No. 5,989,648 to Phillips discloses a method for forming nanoparticle metal catalysts on carriers. However, referring back to FIG. 3, it is important to note that nanoparticles 400 such as the one shown in FIG. 4 are not generally compatible with existing processes for chemical conversion. For compatibility with existing processes, the nanoparticles 400 are bonded to a support. To that end, more steps are taken to bring the nanoparticles 400 to a useable form. In some embodiments, the process 300 continues with step 340, where the nanoparticles 400 are combined with a liquid to form a dispersion 345. Preferably, a liquid that will not react with the PGM or the carrier material is used. Some appropriate liquids are aqueous solutions or organic solutions employing solvents such as alcohols, ethers, hydrocarbons, esters, amines, or the like. Since the nanoparticles 400 are small, other precautions are generally taken to ensure that they suspend evenly within the dispersion. To that end, an adjunct 348 is able to be added to the dispersion. The adjunct 348, also referred to commonly in the art as a surfactant or dispersant, adheres to the nanoparticles 400 and causes them to repel each other, thereby causing the nanoparticles 400 to suspend evenly in the dispersion 345. The dispersion 345 is also referred to as a suspension.

Figure 1:
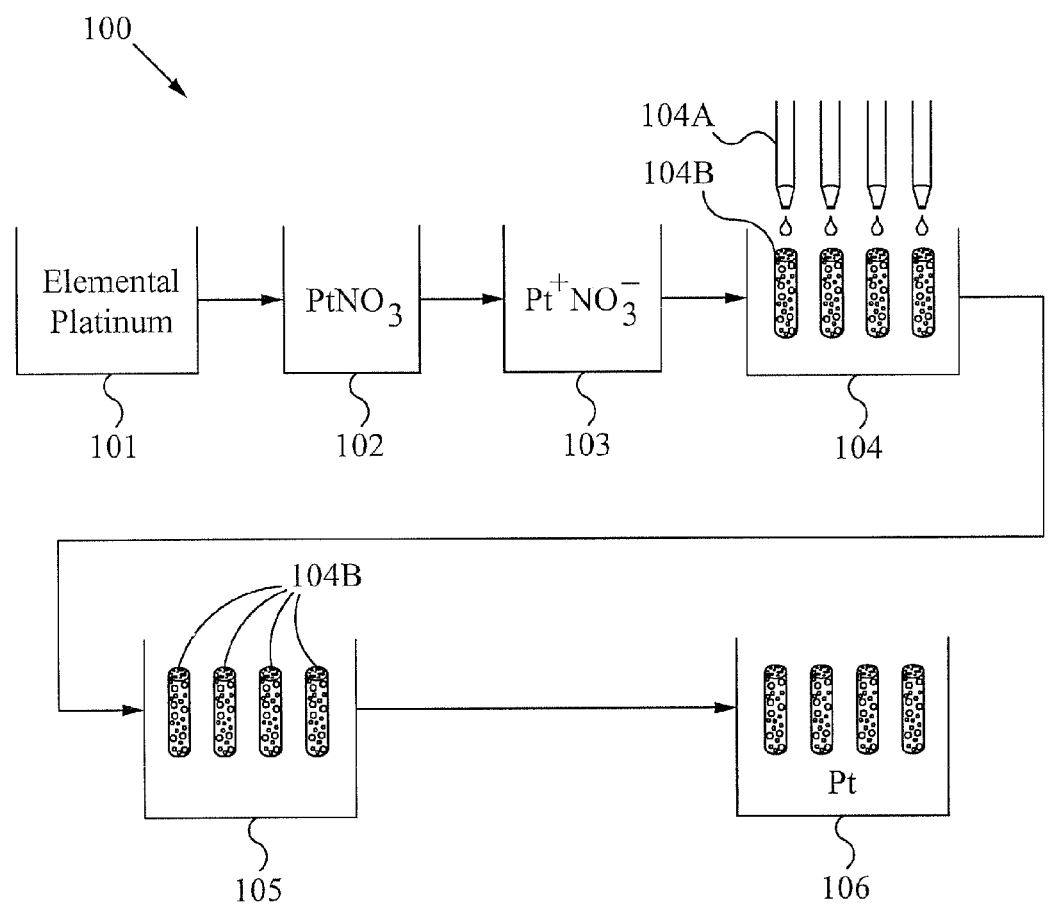
FIG. 1 prior art illustrates an existing process for forming a useful support for use in heterogenous catalysis.
Figure 2:
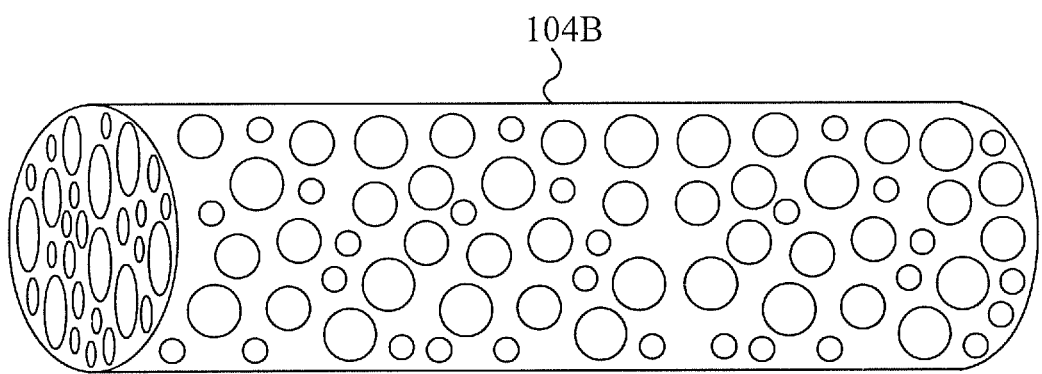
FIG. 2 prior art shows a porous support generally used as a support in heterogeneous catalysis.

To bring the nanoparticles 400 closer to a usable catalyst, the nanoparticles 400 are impregnated onto supports 355. The supports 355 are also known to those skilled in the relevant art as porous oxides. Alternatively, the supports 355 are also referred to as extrudates because they are generally made using an extrusion process. The supports 355 are similar to the supports 104b in FIGS. 1 and 2. Such supports have found utility due to their highly accessible and large surface area, as high as 250 m²/g. In alternative embodiments, a macroscopic support particle is able to be used. In such an embodiment, the size of the macroscopic support particle is selected to provide maximum surface area to which nanoparticles 400 are bonded or fixed. The step 350A shows the preferred embodiment of achieving the impregnation. The dispersion 345 is combined with a quantity of substantially dry porous supports 355A to form a mixture 359A. Alternatively, as shown in the step 350B, the dispersion 345 is combined with a slurry 358 having macroscopic support particles 355B suspended therein, thereby forming the mixture 359B. The slurry 358 is able to be a suspension of water, alcohol, or any suitable organic or inorganic liquid which will not react with the macroscopic supports 355B or nanoparticles 400. In the step 350A, capillary forces will draw in the dispersion 345, and in turn the nanoparticles 400, into the various voids and pores within the structure of the porous supports 355A, thereby forming impregnated porous supports 365A. To aid in the impregnation, the mixture can be agitated or subjected to heat or pressure. In the step 350B, nanoparticles 400 come to rest on the surfaces of macroscopic supports thereby forming impregnated macro supports 365B. In some embodiments, the steps 350A or 350B are repeated at least once for enhanced impregnation.

Figure 4B:
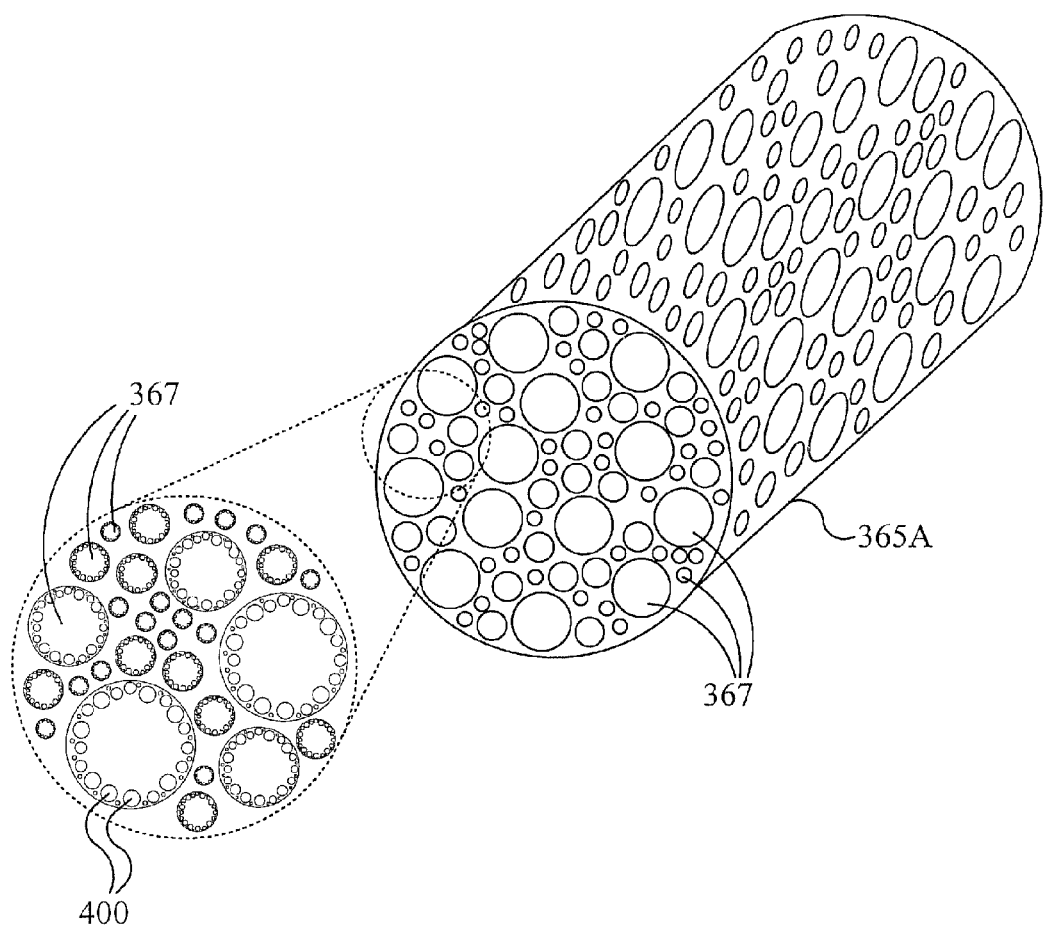
FIG. 4B shows a close up of an impregnated porous support.
Figure 4C:
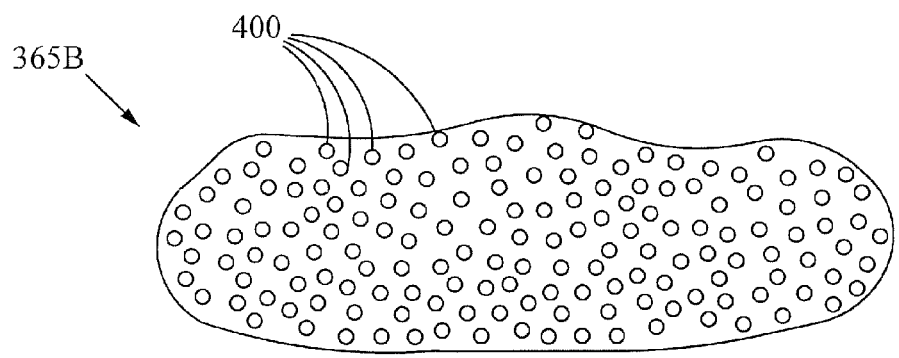
FIG. 4C shows a close up of an impregnated macro support.

Next, in the steps 360A and 360B, the impregnated porous supports 365A or macro supports 365B are allowed to dry. A close up view the impregnated porous support 365A is shown in FIG. 4B. As the liquid in the dispersion 345 evaporates, the nanoparticles 400 settle onto the surface of the support 365A and into the pores 367 within the support 365A. FIG. 4C shows an example of an impregnated macro support 365B. As the liquids in the dispersion 345 and slurry 358 dry, nanoparticles 400 settle onto the surface of the macro support 365B. When the impregnated porous supports 365A or macro supports 365B dry, electrostatic interactions and other forces between the nanoparticles 400 and the porous supports 365A or macro supports 365B effectuate some adhesion. Advantageously, such forces cause the nanoparticles 400 to stick onto the surfaces and pores 367 of the supports 365A or 365B, and effectuate transfer of the supports 365 through the remainder of the process 300. Referring back to FIG. 3, a calcining step 370A or 370B is performed to form oxide-oxide bonds between the carrier portion 410 of the nanoparticles 400 and the impregnated supports 365A or 365B by exposing them to heat 372, pressure 375, or a combination thereof. The calcining temperature is generally from 350 to 1000 degrees centigrade, and the pressure is on the order of ambient atmosphere to several atmospheres. For optimum oxide-oxide bonds, the carrier material 314 is chosen to correspond to the material of which the support 365A or 365B is comprised. By way of example, if the carrier material 314 is alumina, then the support 365A or 364B preferably comprises alumina, although dissimilar oxides are also contemplated. Due to the physical and chemical bond between the supports 365A and 365B and the nanoparticles 400, islands of nanoparticles that are bonded, fixed or otherwise pinned to the surfaces of the supports 365A or 365B will not migrate and coalesce during catalytic conversion. The surface area for catalysis remains high, and therefore the catalytic activity remains high. In effect, operations such as fine chemical plants and oil refineries will not be required to stop operations and swap out ineffective catalyst supports with fresh catalyst supports with the same frequency as existing processes, thereby increasing throughput at the plants and refineries and reducing their overall cost of operation.

Nanopowder with composition 3.4% (w/w) platinum and balance aluminum oxide was produced according to the process of FIG. 3. A vial was charged with 0.5 g of Coatex DV-250 (Coatex), 0.1 g of tris(hydroxymethyl)aminomethane (Aldrich), and 8.9 g of deionized water and shaken to form a solution. To this solution was added 0.5 g of the aforementioned nanopowder. This mixture was sonicated for 30 min using a Sonicator 3000 (Misonix) equipped with a ½" horn operating at 30 W with a 1.0 s on/0.5 s off pulse. The dispersion was cooled with a water ice bath during sonciation. The dispersion was then added dropwise to 1.0 g of alumina extrudates (Alfa Aesar) to incipient wetness –0.45 g of dispersion was required. The impregnated extrudates were then dried at 125° C. for 1 hr. The impregnation and drying steps were then repeated two more times, which required 0.40 g and 0.29 g, respectively, of dispersion to reach incipient wetness. The extrudates were then calcined in air at 550° C. for 2 hr. The platinum content of the extrudates is 0.15% (w/w) by ICP-MS analysis. The morphology of the material consists of mainly <5 nm platinum particles that are bonded to <50 nm alumina particles that are bonded to >1 micron alumina particles as witnessed by TEM analysis. Chemisorption analysis (CO) yielded a 24.1% dispersion, thus proving that the platinum surface is available for chemisorption. The average particle size calculated from chemisorption data is 4.7 nm. Preferably, custom automated systems provide means for actuating the steps of the process 300. Such custom automated systems are widely commercially available and used extensively in the medical, pharmaceutical and chemical industries, among others.

Figure 5:
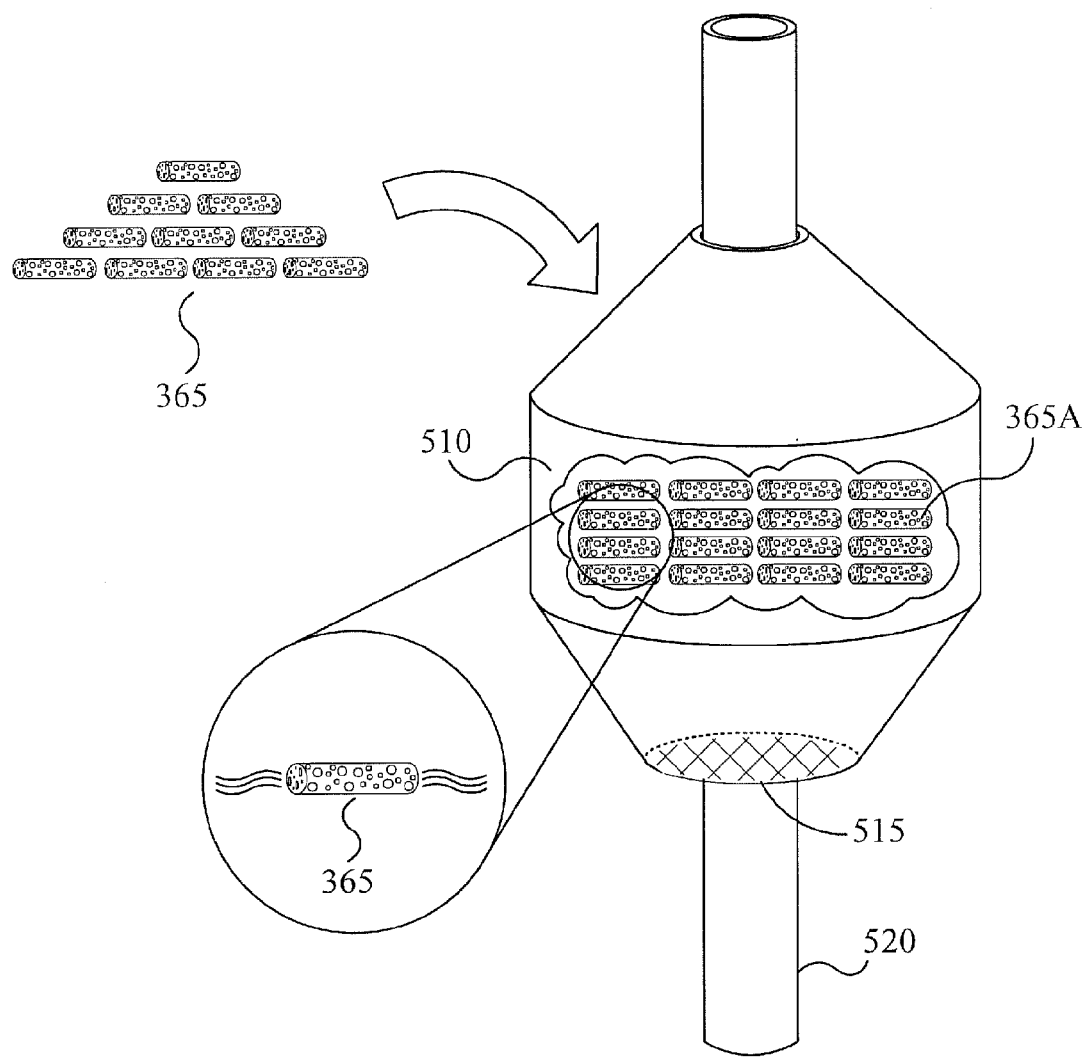
FIG. 5 shows an example of the supports being used as heterogeneous catalysts.

FIG. 5 shows an example of the impregnated porous supports 365A being used in the fine chemical industry to hydrogenate benzene into cyclohexane. Macro supports 365B are able to be used as well. Although this example details use in the fine chemical industry, it will be apparent to those of ordinary skill in the arts of chemistry, chemical engineering, or the like that any process using heterogeneous catalysis is able to benefit from this disclosure. An amount of impregnated porous supports 365A is loaded into a reactor 510. Preferably, the reactor 510 has a mesh opening 515 on one end wherein the meshing has a smaller opening pitch than the size of the supports 365 such that the supports 365 do not fall through the opening 515. Benzene is passed into the reactor 510 via the conduit 520. As the benzene passes through the reactor 510, the benzene fills into the voids and pores of the supports 365A.

Figure 5A:
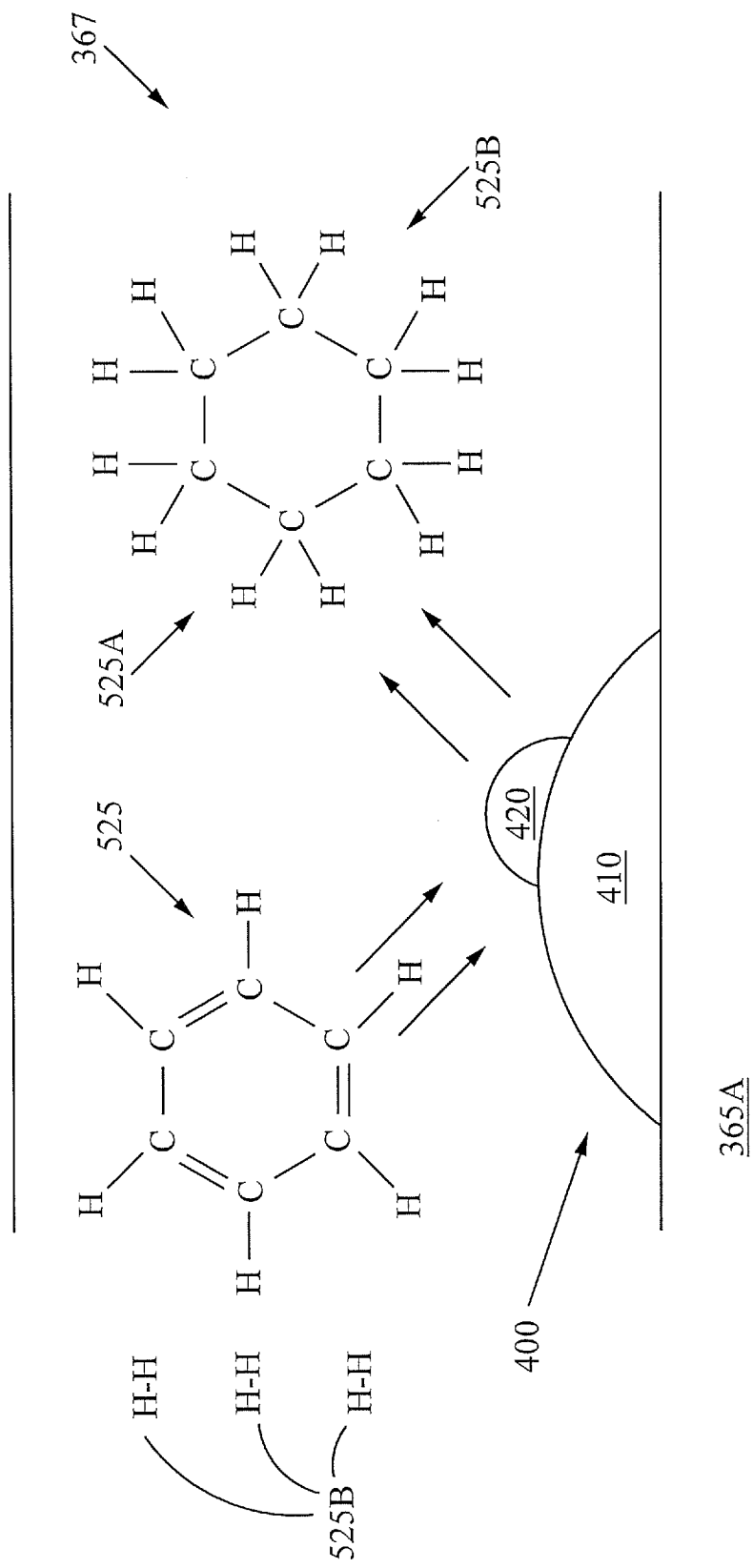
FIG. 5A shows the hydrogenation of benzene into cyclohexane.

FIG. 5A shows an example of a benzene molecule 525 being hydrogenated into cyclohexane 525A in a cross section of a pore 367. When the benzene molecule 525 comes into contact with the catalyst portion 420 of the nanoparticle 400 that is bonded to the surface of the support 365A, the catalyst portion 420 of the nanoparticle 400 will effectuate hydrogenation of the benzene molecule 525 and hydrogen molecules 525B into cyclohexane 525A.

We claim:

1. A system for forming a metal catalyst comprising:
   a. means for providing a quantity of nanoparticles, including means for loading a quantity of catalyst material in powder form and a quantity of carrier in powder form into a plasma gun in a desired ratio, wherein at least a portion of the nanoparticles comprises a carrier portion and a catalyst portion, means for vaporizing the catalyst material and carrier in a reaction chamber, thereby forming a vapor cloud, and a highly turbulent quench chamber configured to quench the vapor cloud thereby forming solid nanoparticles, wherein the highly turbulent quench chamber comprises a frusto-conical body having a wide end, a narrow end, and a quench region formed between the wide end and the narrow end, and a reactive mixture inlet configured to receive the vapor cloud and to supply the vapor cloud into the quench region in the direction of the narrow end, wherein the quench chamber further comprises at least one conditioning fluid inlet configured to supply a conditioning fluid into the quench region in the direction of the narrow end;
   b. means for forming a suspension of the nanoparticles in a liquid; and
   c. means for bonding the nanoparticles to supports such that the carrier portion bonds to the supports and the catalyst portion is exposed to a reaction environment.

2. The system of claim 1 wherein the supports comprise voids and pores.

3. The system in claim 1 wherein the catalyst material comprises any one of at least one metal, at least one metal alloy, and any combination thereof.

4. The system of claim 1 further comprising a dispersant for adhering to the nanoparticles and causing them to repel each other within the suspension.

5. The system of claim 1 further comprising means for drying the supports.

6. The system of claim 1 further comprising means for exposing the supports to heat, pressure, or a combination thereof thereby bonding the nanoparticles onto the supports.

7. The system of claim 1 further comprising a slurry having supports suspended therein.

8. The system of claim 7 wherein the slurry comprises and one of an organic solvent, an aqueous solvent, and any combination thereof.

9. The system of claim 1 wherein the means for combining the suspension with supports comprises means for impregnating supports with the suspension.

10. The system of claim 1 wherein the carrier comprises an oxide.

11. The system of claim 10 wherein the oxide comprises any among a list of silica, alumina, yttria, zirconia, titania, ceria, baria, and any combination thereof.

12. A system for forming a supported nanoparticle catalyst comprising:
    a. a plasma gun for vaporizing a quantity of catalyst material in powder form and a quantity of carrier material in powder form in a first reaction chamber to form vaporized metal catalyst and carrier;
    b. a highly turbulent quenching chamber configured to quench the vaporized metal catalyst and carrier to form bonded nanoparticle catalysts, each bonded nanoparticle catalyst having a carrier portion and a catalyst portion, wherein the highly turbulent quench chamber comprises a frusto-conical body having a wide end, a narrow end, and a quench region formed between the wide end and the narrow end, and a reactive mixture inlet configured to receive the vaporized metal catalyst and carrier and to supply the vaporized metal catalyst and carrier into the quench region in the direction of the narrow end, wherein the quench chamber further comprises at least one conditioning fluid inlet configured to supply a conditioning fluid into the quench region in the direction of the narrow end;
    c. a second reaction chamber for combining the bonded nanoparticle catalysts with a quantity of supports to form supported nanoparticle catalysts; and
    d. drying means for drying the supported nanoparticle catalysts.

13. The system of claim 12 wherein the carrier material comprises an oxide.

14. The system of claim 12 wherein the catalyst material comprises a metal.

15. The system of claim 12 wherein the second reaction chamber is able to expose the supports to heat, pressure, or a combination thereof, to bond the carrier material of the catalyst nanoparticles onto the supports, such that the catalyst portion is exposed to a reaction environment.

16. The system of claim 12 wherein the second reaction chamber comprises a vat for suspending the supports and catalyst nanoparticles in a slurry.

17. The system of claim 12 wherein the support comprises the same material as the carrier material.

18. The system of claim 1 further comprising means for repelling the nanoparticles in the liquid.

* * * * *